United States Patent [19]

Waterbury et al.

[11] Patent Number: 4,861,721
[45] Date of Patent: Aug. 29, 1989

[54] BACTERIA FOR CELLULOSE DIGESTION

[75] Inventors: John B. Waterbury, Woods Hole; Charles B. Calloway, Shrewsbury; Ruth D. Turner, Cambridge, all of Mass.

[73] Assignee: Research Corporation, New York, N.Y.

[21] Appl. No.: 654,336

[22] Filed: Sep. 25, 1984

[51] Int. Cl.$^4$ .......................... C12N 1/20; C12P 21/00
[52] U.S. Cl. ..................................... 435/252.1; 435/68
[58] Field of Search ................... 435/243, 253, 68, 99, 435/209, 804, 105, 252.1

[56] References Cited

U.S. PATENT DOCUMENTS

| | | |
|---|---|---|
| 3,764,475 | 10/1973 | Mandels et al. |
| 4,104,124 | 7/1978 | Srinivasan et al. |
| 4,278,766 | 6/1981 | Srinivasan et al. |
| 4,366,245 | 12/1982 | LaLonde |
| 4,405,715 | 9/1983 | Monsan ............................. 435/105 |
| 4,439,523 | 3/1984 | Malick et al. |
| 4,439,525 | 3/1984 | Shay et al. |

OTHER PUBLICATIONS

Waterbury et al., "A Cellulolytic Nitrogen-Firing Bacterium Cultured from the Gland of Deshayes in Shipworms (Bivalvia: Teredinidae", *Science*, vol. 221 (1983) pp. 1401-1403).
Barman, *Enzyme Handbook*, vol. 2, Springer-Verlag New York, Inc., N.Y. (1969) pp. 565-566.
Suzuki et al., "Extracellular and Cell-bound Cellulase Components of Bacteria", *Cellulases and Their Applications*, A.C.S., Washington, D.C. (1969) pp. 60-82.
Mandels et al., "The Production of Cellulases", *Cellulases and Their Applications*, A.C.S., Washington, D.C. (1969) pp. 391-414.
Mandels, M., et al., *Advan. Chem. Ser.*, vol. 23, pp. 391-413, 1969.
Suzuki, H., et al., *Advan. Chem. Ser.*, vol. 6, pp. 60-82, 1969.
Ghose, T. K., *Advan. Biochem. Engng.*, vol. 6, pp. 39-74, 1977.
Gong, Cheng-Shung, et al., *Advan. Biochem. Engng.*, vol. 20, pp. 93-118, 1981.
Rippka, R., et al., *Journal of General Microbiology*, vol. 111, pp. 1-61, 1979.
Trytek, R. E., *Comp. Biochem. Physiol.*, vol. 67 A, pp. 419-427, 1980.
Popham, J. D., et al., *Marine Biology*, vol. 19, pp. 338-340, 1973.
Hardy and Silver, eds., "A Treatise on Dinitrogen Fixation", Section III Biology pp. 6-8, 46 A Wiley-Interscience Publication, John Wiley and Sons Press, N.Y., 1977.
Sigerfoos, C. P., *Bull. Bur. Fish.*, vol. 27, pp. 191-233, 1908.
Davis, H. C., et al., *Fish. Rev. Bull.*, vol. 58, pp. 293-304, 1958.
Morton, B., *Oceanogr. Mar. Biol. Ann. Rev.*, vol. 16, pp. 107-144, 1978.
Gong, Cheng-Shung, et al., *Ann. Rep. on Ferm Proc.*, vol. 3, pp. 111-140, 1979.

*Primary Examiner*—Blondel Hazel
*Attorney, Agent, or Firm*—Scully, Scott, Murphy & Presser

[57] ABSTRACT

This invention relates to a process for the microbial degradation of cellulosic material. More specifically, this invention relates to a process for the digestion of cellulose by a microbe capable of carrying out the cellulolytic activity in the presence or absence of combined nitrogen.

1 Claim, 2 Drawing Sheets

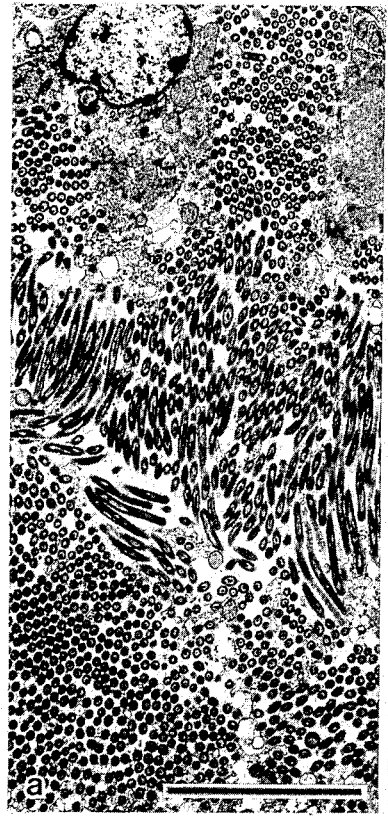
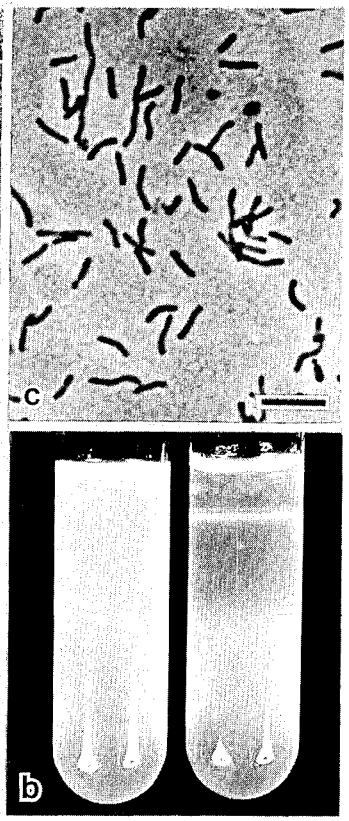
FIG. 1c
FIG. 1a FIG. 1b

BACTERIA FOR CELLULOSE DIGESTION

This invention was made with support in part by Office of Naval Research Contracts N00014-76-C-0281 and NR 104-687 and by National Science Foundation grant OCE80-25241.

FIELD OF THE INVENTION

This invention relates to a process for the microbial degradation of cellulosic material. More specifically, this invention relates to a process for the digestion of cellulose by a microbe capable of carrying out the cellulolytic activity in the presence or absence of combined nitrogen.

BACKGROUND OF THE INVENTION

Cellulose is a linear polymeric molecule comprised of D-glucose units bonded by $\beta$-1,4-glucosidic linkages. The degree of polymerization (based on D-glucose) can range up to 30,000 or more. Common sources of cellulose include cotton containing approximately 90% cellulose and wood containing generally about 45% cellulose. Cellulose represents the most abundant, renewable organic material on earth. This readily available resource has been considered as potentially valuable as a starting material for the production of food, fuel and chemicals. One important approach has been the isolation and characterization of enzymes capable of degrading cellulose to provide glucose. These enzymes denominated as cellulases have been the subject of several recent review articles (Ghose, T. K., In: "Adv. in Biochem. Eng", Fiechler, Acd., Springer-Verlag. Berlin (1977) and Gong, C. S. et al. In: "Ann. Rev. of Ferment. Proc.", Perlman, D. ed. Academic Process, New York (1979)). It should be noted that cellulase as used herein refers to a group of enzymes which catalyze the hydrolysis of the $\beta$-1,4-linkages of the cellulose substrate. Three components of the enzyme system have been recognized and each has been designated by a variety of names by workers in the field. The first component, hypothesized to modify native cellulose of high crystallinity, thus rendering it more susceptible to further degradation, is referred to as $\beta$-glucan cellobiohydrolase and also known as $C_1$, exoglucanase, exocellulase, avicelase, or cellobiohydrolase. The second component, believed to be responsible for the majority of the degradation reaction, is referred to as $\beta$-glucan glucanohydrolase and also known as $C_x$, endoglucanase, endo-$\beta$-glucanase or CMCase. The third component which catalyzes the hydrolysis of cellobiose to glucose, is referred to as $\beta$-glucosidase and also known as cellobiase.

The biological reduction of $N_2$ (dinitrogen) to ammonia is known as 'diazotrophy, or biological nitrogen fixation. This biological process is unique to procaryotic organisms amongst which it is relatively widespread. The enzyme system responsible for this process is known as the nitrogenase system. It is similar in all the bacteria examined to date and consists of two components; dinitrogenase (the molybdoprotein) and dinitrogenase reductase (the iron protein). (See for example J. R. Postgate, "The fundamentals of nitrogen fixation," 1982, Cambridge University Press, Cambridge).

As the references above indicate, cellulases from a variety of organisms have been studied with respect to their potential uses in industrial processes. Likewise, diazotrophy (nitrogen-fixation) is of considerable industrial and agricultural importance. It is the object of the invention to provide a bacterium that is capable of both cellulose digestion and nitrogen fixation. A bacterium has been isolated from the gland of Deshayes in teredinid molluscs and is novel because it is the first bacterium known to both digest cellulose and fix nitrogen.

The wood-boring shipworms make up a group of bivalve molluscs known as the Teredinidae. These economically important molluscs have received considerable notoriety both historically and presently because of the damage they cause to wooden ships and timber structures in seawater. They are abundant globally and especially prevalent in the tropics, with 14 genera and 67 species currently recognized.

The gland of Deshayes is unique to the Teredinidae. It was discovered more than a century ago by Deshayes (Deshayes, G. P. *Explor. Sci. d'Alger. Zool.* 1: 35 (1848)) and subsequently named and described by Sigerfoos (Sigerfoos, C. P., *Bull. Bur. fish.* 27: 191 (1908)). To date, functions ascribed to this gland have been inferred largely from circumstantial evidence. They include the production of cellulolytic enzymes (Morton B., *Oceanogr. Mor. Biol.* 16: 107 (1978)) and the synthesis of amino acids (Trytek, R. E. et al. *Comp. Biochem. Physiol.* 67: 149 (1980)). The gland consists of a brown, irregular mass or tissue lining the gill lamellae. Two ducts, one for each gill lie laterally adjacent to the gland in the afferent branchial vein and extend from the posterior to the anterior portion of the gill where they appear to join the esophagus. Popham and Dickson (Popham J. D. et al. *Mar. Biol.* 19: 338 (1973)) using transmission electron microscopy showed in several species of shipworms that the gland contains numerous rodshaped, Gram-negative bacteria.

BRIEF DESCRIPTION OF THE INVENTION

This invention provides a microorganism isolatable from the gland of Deshayes in a member of the Teredinidae, said microorganism being further characterized by an ability to degrade cellulose in the presence and the absence of combined nitrogen. Combined nitrogen is defined as forms of inorganic and organic nitrogen that are combined with other elements.

In a further embodiment the invention provides a method for isolating a cellulose-degrading microorganism from the gland of Deshayes comprising
 (a) dissecting said gland from a member of the family Teredinidae,
 (b) washing the dissected gland in sterile sea water,
 (c) homogenizing the washed gland,
 (d) establishing cultures by serial dilution of the gland homogenate in a mineral selective medium and
 (e) recovering individual isolates by streaking on to a solid medium supplemented with a source of combined nitrogen.

In yet another embodiment the invention provides a method for the production of single cell protein which comprises culturing under microaerophilic fermentation conditions in the absence of combined nitrogen employing cellulose in a mineral salts medium, a microorganism isolated from the gland of Deshayes capable of degrading cellulose in the presence and absence of a source of combined nitrogen and recovery of the resulting cellular products as a single cell protein material.

In yet another embodiment this invention provides a method for producing cellulase which comprises culturing the microoganism isolated from the gland of Deshayes capable of degrading cellulose in the presence and absence of a source of combined nitrogen in a suitable culture medium.

In yet another embodiment this invention provides an enzyme having cellulase activity when produced by the microorganism isolated from the gland of Deshayes capable of degrading cellulose in the presence and absence of a source of combined nitrogen.

In yet another embodiment this invention provides a method of degrading cellulose comprising contacting cellulose with the enzyme isolated from a microorganism isolated from the gland of Deshayes capable of degrading cellulose in the presence and absence of a source of combined nitrogen under cellulolytic conditions.

In a final embodiment the invention provides a method for digestion of cellulose comprising contacting cellulose with a microorganism isolated from the gland of Deshayes under cellulolytic conditions in the presence or absence of combined nitrogen.

DETAILED DESCRIPTION OF THE FIGURES

Figure 2:
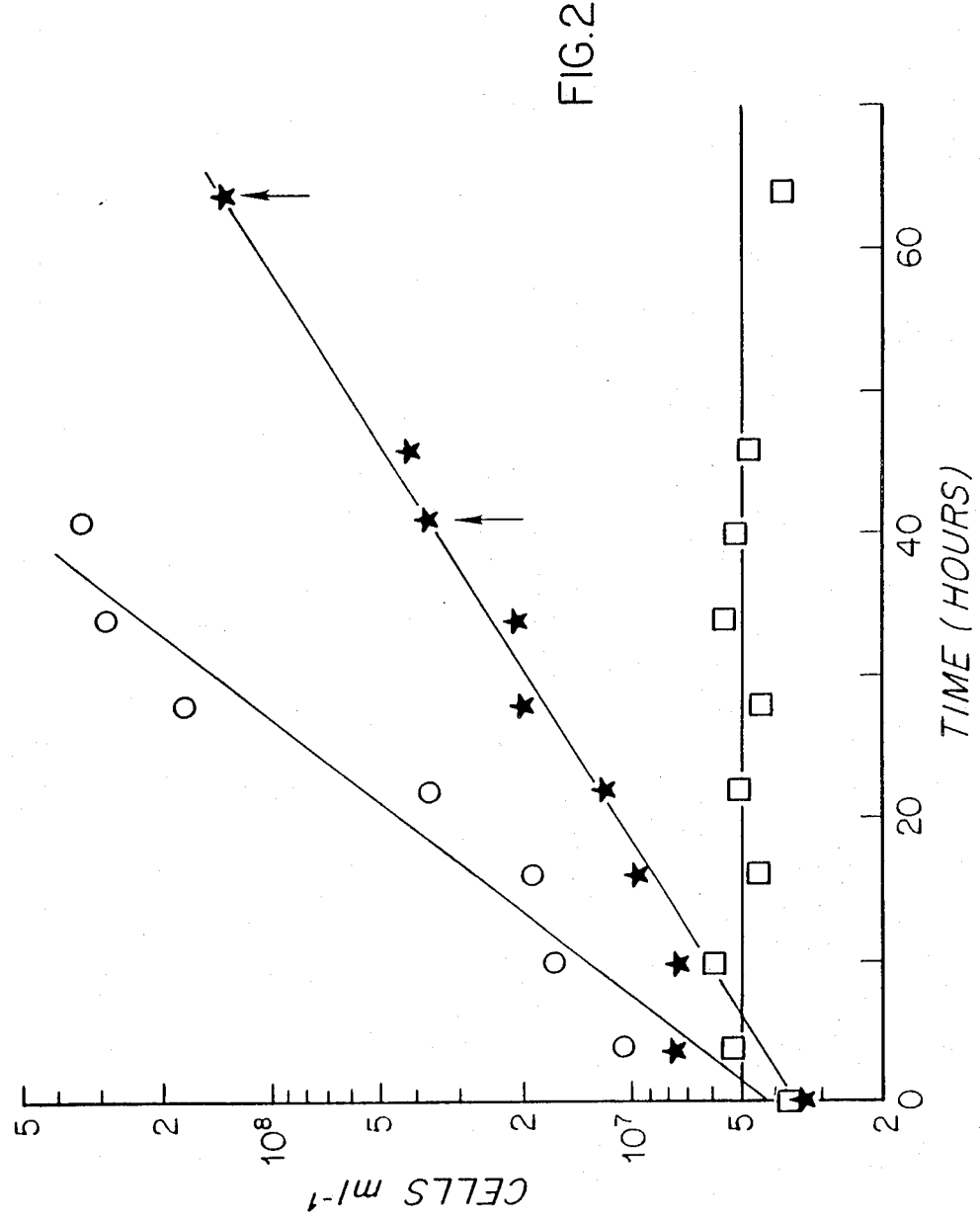

FIG. 1a is a transmission electron micrograph of a thin section of the gland of Deshayes from *Lyrodus pedicellatus*, showing numerous Gram-gegative, rod-shaped bacteria. Scale bar, 5 um.

FIG. 1b is a photograph showing a bacterial isolate *Lyrodus pedicellatus* growing on colloidal cellulose agar medium (tube on right). The distinct band of cells below the agar surface and the disappearance of the colloidal cellulose both above and below this band should be noted. The tube at left contains uninoculated medium; the colloidal cellulose is uniformly distributed.

FIG. 1c is a phase contrast photomicrograph of the bacterium isolated from the gland of Deshayes of *Lyrodus pedicellatus*. Scale bar 5 um.

FIG. 2 illustrates the growth of bacterial isolate from *Lyrodus pedicellatus* at 35° C. in an atmosphere of nitrogen plus 1.0 percent $O_2$ and 500 ppm $CO_2$ in liquid basal medium. (□) Control culture containing 5 mM ammonium chloride but no carbon source. (O) Culture containing powdered cellulose and 5 mM ammonium chloride. (*) Culture containing powdered cellulose but no combined nitrogen. Arrows show when samples were withdrawn for measurement of acetylene reduction. Ethylene was produced at 23 and 24 nanomoles per milligram of protein per minute at hours 41 and 64, respectively.

DETAILED DESCRIPTION OF THE INVENTION

This invention relates to a bacterium isolated from the gland of Deshayes of shipworms and the use of said bacterium in a variety of industrially important processes.

To isolate the bacterium from the gland of Deshayes, the gland was dissected from individual shipworms that had been removed from wooden panels and washed in sterile sea water. The gland and associated gill tissue were then washed several times in sterile seawater and homogenized. Cultures were established by serial dilution in a mineral selective medium composed of the following: filtered seawater (750 ml/liter), double-distilled water (250 ml/liter), $K_2HPO_4$ (15.3 mg/liter), $Na_2CO_3$ (10 mg/liter). $Na_2MoO_4\text{-}2H_2O$ (2.5 mg/liter), disodium EDTA (0.5 mg/liter), ferric ammonium citrate (brown crystals) (3 mg/liter) citric acid (3 mg/liter), Hepes buffer (pH 8.0)(5.206 g/liter) A-5 trace metals (1.0 ml/liter) [R. Rippka J. Deruelles J. Waterbury, M. Herdman R. Stanier, *J. Gen. Microbiol* 111: 1 (1979)], and Va vitamin mixture (0.2 ml/liter) [H. C. Davis and R. R. L. Guilard, *Fish Rev. Bull.* 58: 293 (1958)], supplemented with 0.2 percent agar, with powdered cellulose (SIGMACELL TYPE 100; SIGMA) as the source of carbon and energy and no source of combined nitrogen. Growth appeared as a sharply defined lens of cells about 1 cm below the agar surface (FIG. 1b). Cells for isolation were removed from the tubes of greatest dilution (typically between $10^7$ and $10^8$ dilution) and streaked onto a solid medium (0.9 percent agar) made of the mineral base with powdered cellulose and ammonium chloride (5 mM). Axenic stock cultures were maintained in tubes of basal medium containing 0.2 percent agar, with cellulose as the carbon and energy source and no source of combined nitrogen.

The bacterium may be isolated from a variety of taxa within the family Teredinidae throughout the world. Table 1 shows the variety of species of shipworms and the location from which the bacterium of the subject invention was isolated.

The bacterium has been isolated from 6 genera and 15 species of the currently recognized 14 genera and 67 species within the family Teredinidae (Table 1).

Surprisingly, the bacterial isolates from the 15 species are similar and likely represent a single species. This indicates that the bacterium will be present in the gland of Deshayes in all members of the Teredinidae, a contention that is supported by the fact that the bacterium has been successfully isolated from every species of shipworm so far examined.

TABLE I

Sources of Cellulolytic Nitrogen-Fixing Bacteria

| Shipworms | Origin |
|---|---|
| *Teredo navalis* (Linnaeus) | Woods Hole, MA |
| *T. furcifera* (Von Martens) | Bermuda |
| *T. bartschi* (Clapp) | Bermuda |
| *Lyrodus pedicellatus* (Quatrefages) | Long Beach, CA |
| *L. bipartitus* (Jeffreys) | Fort Pierce, FL |
| *Bankia gouldi* (Bartsch) | Beaufort, NC and Fort Pierce, FL |
| *B. rochi* (Moll) | Karachi, PAKISTAN |
| *B. fimbriatula* (Moll and Roch) | Fort Pierce, FL |
| *B. setacea* (Tryon) | Friday Harbor, WA |
| *B. fosteri* (Clench and Turner) | Floating wood, Deep Ocean Station #2 (DOS-2) 38° N 69° W |
| *B. carinata* (Gray) | Floating wood, Deep Ocean Station #2 (DOS-2) 38° N 69° W |
| *Teredora malleolus* (Turton) | Floating wood, Deep Ocean Station #2 (DOS-2) 38° N 69° W |
| *Nototeredo knoxi* (Bartsch) | Floating wood, Deep Ocean Station #2 (DOS-2) 38° N 69° W |
| *N. edax* (Hedley) | Waltair Harbor, INDIA |
| *Psiloteredo healdi* (Bartsch) | Lake Maricaibo, VENEZUELA |

The bacterium is a Gram-negative rigid rod, 0.4 to 0.6 um wide and 3 to 6 um long (FIG. 1c) that moves by means of a single polar flagellum. In stationary phase cultures the cells often become pleomorphic appearing spiraled or as very long rods. The guanine plus cytosine content of the DNA ranges from 49 to 51 mole percent G+C.

This bacterium is an aerobic chemoheterotroph that will grow in a simple mineral medium containing seawater and a suitable source of organic carbon. It requires a source of combined nitrogen if vigorously aerated but will fix molecular nitrogen, as documented by the acetylene reduction method (Hardy, R. W. F. et al. In: "A Treatise on Dinitrogen Fixation" Hardy R. W.

eds. Wiley, New York (1977)), when grown under microaerophilic conditions. It is obligately marine, requiring elevated concentrations of $Na^+$, $Cl$, $Mg^2$ and $Ca^{2+}$ for growth; Growth has been demonstrated by using the following compounds as sole carbon and energy sources: cellulose (Whatman No. 1 filter paper or SIGMACELL 100), carboxymethyl cellulose (0.5 percent weight to volume), fructose (0.5 percent), sucrose (0.5 percent) acetate (0.1 percent), pyruvate 0.1%, succinate (0.1 percent) and glutamate (0.1 percent). The optimum temperature for growth is 35° C.; growth is absent at 39° C. Specific growth rates measured at 35° C. by using powdered cellulose in the presence or absence of combined nitrogen are 0.12 and 0.05 per hour, respectively (FIG. 2). These bacterial isolates appear to be unique, fitting into none of the known genera of bacteria.

A deposit of a biologically pure culture of the bacterium was made with the American Type Culture Collection, 12301 Parklawn Drive, Rockville, Md., the accession number ATCC 39867 was assigned and the requisite fees were paid. Access to said culture will be available during pendency of the patent application to one determined by the Commissioner to be entitled thereto under 37 C.F.R. §1.14 and 35 U.S.C. §122. All restriction on availability of said culture to the public will be irrevocably removed upon the granting of a patent based upon the captioned application and said culture will remain permanently available during the term of said patent; and should the culture become nonviable or be inadvertently destroyed, it will be replaced with viable culture(s) of the same taxonomic description.

Three lines of evidence indicate that the bacterium isolated is the bacterium present in the gland of Deshayes. First, precautions were taken to minimize contamination during removal of the gland and subsequent isolations were made from serial dilutions after a $10^7$ or $10^8$ dilution of gland homogenate. Using these procedures, it is possible to repeatedly isolate the same bacterium from a number of different animals of a single species as well as from fifteen different species collected and maintained at different locations. Conversely, it is not possible to isolate the bacterium from either seawater or the normal wood flora. Second, the very uniqueness of the physiology of all the bacterial isolates, that is, the ability to degrade cellulose and fix nitrogen argues against their being chance contaminants. Finally the bacterium in the gland of Deshayes is morphologically distinct. The isolates are morphologically similar both to the bacterium in the gland and to each other.

The bacterium from the gland to Deshayes possesses two properties, cellulose digestion and nitrogen fixation, that genetic engineers have been trying (unsuccessfully) to combine in a single bacterium. The combination of these properties in this bacterium makes it useful for producing single-cell protein from cellulose without the necessity of adding combined nitrogen. Further, the organism of this invention may be used as a source of cellulase useful for the degradation of cellulose. A further embodiment comprises the use of this organism in a process for the production of organic acids and other metabolic products of glucose metabolism from cellulosic starting materials with or without the necessity of adding combined nitrogen.

What is claimed is:

1. A biologically pure culture of a microorganism isolatable from the gland of Deshayes of a member of the Teredinidae, said microorganism being a Gram-negative rigid rod-shaped bacterium, possessing a single polar flagellum, and a guanine plus cytosine content in the DNA of 49 to 51 mole percent, having the identifying characteristics of ATCC No. 39867, and genetic derivatives thereof, and being further characterized by an ability to degrade cellulose in the presence and the absence of combined nitrogen.

* * * * *